United States Patent [19]

Steinman

[11] Patent Number: 5,397,710
[45] Date of Patent: Mar. 14, 1995

[54] PROCESS FOR MEASURING MAGNESIUM IN BIOLOGICAL FLUIDS

[75] Inventor: Gary D. Steinman, Holliswood, N.Y.

[73] Assignee: David Diagnostics, Inc., Astoria, N.Y.

[21] Appl. No.: 949,531

[22] PCT Filed: Oct. 2, 1992

[86] PCT No.: PCT/US92/08557

§ 371 Date: Nov. 5, 1992

§ 102(e) Date: Nov. 5, 1992

Related U.S. Application Data

[63] Continuation-in-part of Ser. No. 783,131, Oct. 28, 1991, abandoned.

[51] Int. Cl.$^6$ ............................................. G01N 33/52
[52] U.S. Cl. .................................... 436/79; 427/2.13; 436/164; 436/169; 436/171; 436/176; 422/56
[58] Field of Search ...................... 422/55–61; 427/2; 436/18, 74, 79, 164, 166, 169, 171, 176, 178, 903

[56] References Cited

U.S. PATENT DOCUMENTS

| | | | |
|---|---|---|---|
| 3,798,000 | 3/1974 | Helger | 436/79 |
| 4,215,995 | 8/1980 | Turk et al. | 23/230 R |
| 4,303,610 | 12/1981 | Sardisco et al. | 422/61 |
| 4,386,053 | 5/1983 | Motobayashi | 422/56 |
| 4,425,427 | 1/1984 | Luderer | 435/10 |
| 4,753,890 | 6/1988 | Smith-Lewis et al. | 436/74 |
| 4,966,784 | 10/1990 | Tanaka et al. | 427/2 |
| 5,089,420 | 2/1992 | Albarella et al. | 436/66 |
| 5,215,922 | 1/1993 | Artiss et al. | 436/16 |

OTHER PUBLICATIONS

Schwarzenbach et al., "Komplexone X. Erdalkalikomplexe von o,o'Dioxyzofarbstoffen," *Helvetica Chemica ACTA*, vol. XXXI, Ed. III (1948).

"Spectrophotometric Determination of Small Amounts of Magnesium and Calcium Employing Calmagite," F. Ingman and A. Ringbom, *Microchemical Journal*, 10, 545–553 (1966).

Kodak Clinical Products brochure "Kodak Ektachem DT Slides" released Aug., 1991.

"Dry Reagent Chemistries," B. Walter, *Analytical Chemistry*, 1983, 55, 498A.

*Primary Examiner*—David A. Redding
*Attorney, Agent, or Firm*—Collard & Roe

[57] ABSTRACT

A process for rapidly and conveniently measuring the magnesium concentration of a biological fluid, such as blood or urine, is carried out by fixing amounts of a chelatometric dye, metal cation masking agents, a chelating agent, an alkaline buffer, and a stabilizer on a bibulous material covered with a semipermeable membrane, adding the test specimen, and measuring the amount of color change of the dye at a selected wavelength. The amount of color change is proportional to the quantity of magnesium in the original specimen and can be measured by visual comparison to a standard color chart or with a dedicated reflectance photometer. Furthermore, a method is given for expanding the range of linearity. The method for making the dry indicator includes coating bibulous material with a reaction solution which is dried thereon, followed by coating this material with an organic solution which is dried thereon. The dry indicator composition includes a dihydroxy complexometric dye, a masking agent, a stabilizer, an alkaline buffer, a chelating agent, and a bibulous material.

21 Claims, 1 Drawing Sheet

REFLECTANCE (640 nm)

PROCESS FOR MEASURING MAGNESIUM IN BIOLOGICAL FLUIDS

CROSS REFERENCE TO RELATED APPLICATION

This is a continuation-in-part patent application of U.S. patent application Ser. No. 07/783,131, filed Oct. 28, 1991, now abandoned.

The present invention relates to the preparation of a testing methodology utilizing a chemical reaction for the colorimetric measurement of magnesium in biological fluids, such as blood or urine. More particularly, it relates to a stabilized complexometric reaction in alkaline buffer that determines magnesium concentration by color change in a dry chemistry strip format amenable to performance at the bedside or in the office.

The body of an adult contains 20–30 grams of magnesium, of which 5% is in the extracellular fluids such as blood plasma. Magnesium, compared to other cations, ranks fourth in plasma quantity after sodium, potassium and calcium. Magnesium influences the stability and osmotic equilibrium of cell membranes. This bivalent metal also activates several enzymes concerned with energy transfer. In particular, it is involved with the correct functioning of Na+/K+ ATPase of the neuron membrane and thereby has a protecting function against spontaneous depolarization and neuronal excitability, especially at the neuro-muscular junction.

Magnesium in pharmacological doses has a curariform action on the neuro-muscular junction. Magnesium sulfate has been used for a number of years in obstetrical practice in two clinical situations. First, it is the drug of choice to prevent seizures in preeclampsia. Second, in premature labor or uterine hyperstimulation, magnesium is used for tocolysis. The biggest problem is that the therapeutic serum level is close to the toxic level. The normal range for magnesium in serum is 1.3–2.1 meq/L. The ideal therapeutic level in treating preeclampsia is 6–8 meq/L. However, deep tendon reflexes become hypoactive at 8–10 meq/L and respiratory paralysis develops at 13–15 meq/L.

Most clinicians monitor the patient using reflexes, respiration, and urine output as parameters. Deep tendon reflexes and respirations need to be monitored hourly, and urine output should exceed 100 ml every 4 hours. A more meaningful standard of care would be achieved if the actual serum magnesium level could be determined rapidly and directly. However, the methods now available are not practical for the usual clinical setting since they require timely transport of blood specimens to a central laboratory, careful manipulation of the specimen and execution of the methodology, and report of results back to the delivery suite, all of which may take hours to complete. These results commonly become available long after their clinical pertinence has ceased.

Thus, the instant invention represents an important advance in the treatment of two major therapeutic problems in obstetrics, namely, preeclampsia (toxemia) and premature labor. In these situations magnesium sulfate is the drug of choice. However, because of its toxic potential, this agent needs to be monitored closely and frequently. Heretofore, in the absence of a convenient method for expeditiously testing patients at the bedside, no means have been available to fine tune, on an ongoing basis, the management of conditions which change quickly and frequently. Indirect testing created the possibility of undertreatment or overtreatment, both of which had serious, undesirable consequences. On the other hand, the instant invention now permits the frequent, rapid testing of the blood magnesium level where it is most immediately needed, under the control of the obstetrician at the bedside.

Other than atomic emission spectroscopy, the usual methods now used for determining magnesium in biological specimens involve chelatometry. The original technique involved titration with chelating agents and pH electrodes. This was improved by the advent of the colored indicator methods of Schwarzenbach in 1948 (Helv. Chim. Acta, 31:678), whereby dyes bearing chelatable dihydroxy functions were included. Such dyes either marked the end point of the titration or were in fact the bidentate complexometric agents acting to bind all of the bivalent cations present in the test specimen, thus allowing a direct photometric determination.

As noted above, the methods for serum magnesium determination available now are not suitable for use at the obstetrical bedside, where they are most acutely needed. In addition to the points listed earlier, the chelate dyes suffer from marked instability in alkaline solution, wherein their use in magnesium measurement must be executed because of the pH/color variation characteristics of these reagents. Thus, once test reactants are mixed, they need to be used in a matter of a few hours or days.

U.S. Pat. No. 4,386,053, to Motobayashi, reviews the prior use of boric esters to retard the premature reaction of hydroperoxide and the indicator in a hemoglobin-detecting test system. This is different from the instant invention, which does not employ hydroperoxide, does not test a redox reaction, and does include boric acid.

U.S. Pat. No. 5,089,420, to Albarella similarly describes a method for detecting hemoglobin which uses amine borate complexes for the purpose of blocking the same mutual incompatibility of the two reagents, as Motobayashi sought to effect. In neither case is a cation-detecting indicator employed or is stabilization of a magnesium-sensitive chelatometric reagent even suggested. Neither method uses a dihydroxy indicator, suggesting a different mechanism for stabilization than in the instant invention. Both boric esters and boron amines are known to be strong reducing agents in aqueous solution, whereas boric acid is not. For example, boric esters react with peroxide to give peroxoboric acid solutions which are thought to probably contain the monoperoxoborate anion. Thus, the borate compounds in the Motobayashi and Albarella methods most likely act to synthesize intermediates in the color reaction of interest, rather than as reagent stabilizers, as in the instant invention. Furthermore, the only known chelate complexes of boron have the ring joined through two oxygen atoms in compounds with two replaceable hydrogens. Thus, the mechanism proposed in the instant specification for the stabilization of the chelatometric reagent by boron ring formation is not suggested by these prior art references.

U.S. Pat. No. 4,215,995, to Turk, has included boric acid as a color stabilizer. This is taken to mean stabilization of the final color which results from the intended reaction, rather than stabilization of the test reagents, since color fading is a common problem in some dry chemistry procedures.

U.S. Pat. No. 4,966,784, to Tanaka has used Xylidyl Blue ®, a colorimetric reagent long known for its ability to detect magnesium, among other analytes. In effect, Tanaka has opened standard chemistry textbooks and copied the details of all buffers equally providing the desired pH, only one of which happens to include borate. Nowhere in this patent is the reagent stabilization benefit recognized or taught. In fact, Tanaka finds the only additional benefit of borate to be as an aid to hardening of the gelatin carrier.

It is not possible to expect Xylidyl Blue® 1R (of Tanaka) to interact with borate in the same way as Calmagite® will interact. This is because Applicant previously had independently tested Magon® (Xylidyl Blue II), another chelatometric reagent closely related to that of Tanaka, to be much less stabilized by borate than is Calmagite®. (See the Comparative Example below.)

U.S. Pat. No. 4,753,890, to Smith-Lewis, does not incorporate boric acid to stabilize a color reagent. Similarly, the dry chemistry commercial product that resulted from Smith-Lewis (see Kodak publication C-349) is far from stable, since it must be stored in a freezer before use and used within 15 minutes of package opening. Also, this color reagent is from a completely different class of compounds than Calmagite®. Thus, the potential stabilization attributes of borate were not obvious in view of Smith-Lewis, since this patent clearly teaches a major lack of stability.

It is an object of the present invention to provide a dry chemistry method to measure magnesium in blood serum in a convenient but accurate way amenable to use at the bedside where appropriate changes in patient therapy can be quickly made as needed. The components of the test must be premixed and stable before use, and the dry method is simple enough to be employed by the busy obstetrician without multiple steps for measurement, dilution, separation, calibration, and execution. It is also desirable for this dry method to be inexpensive and to make use of types of instrumentation already available.

The present invention is directed to a process for dry measuring the magnesium concentration of a biological fluid test sample with a dry indicator bibulous material, comprising the steps of: a) providing a dry indicator bibulous material having predetermined effective amounts of a dihydroxy complexometric dye, a masking agent, a chelating agent, and a dryable stabilizer in an alkaline buffer dried onto said material; b) providing a semipermeable membrane for said dry indicator bibulous material able to remove cells and large proteins from a test sample; c) contacting a biological fluid test sample with said dry indicator bibulous material; d) measuring the degree of color change of the dye in said dry indicator bibulous material due to the test sample; e) comparing the degree of color change against results with samples of known amounts of magnesium; and f) then determining the magnesium concentration of said biological fluid test sample.

The present invention is also directed to a process for making a bibulous material dry indicator composition for measuring the magnesium concentration of a biological fluid in a dry chemistry procedure, comprising the steps of: (a) preparing a reaction solution by supplying predetermined effective amounts of a dihydroxy complexometric dye, a masking agent, a chelating agent, and a dryable stabilizer in an aqueous alkaline buffer; (b) dipping the bibulous material into the reaction solution prepared as in step (a); (c) removing said bibulous material from said reaction solution; (d) air-drying said treated bibulous material; (e) dipping said bibulous material into an organic solution containing an organic polymer or a cellulose derivative; (f) removing said bibulous material from said organic solution; and (g) air-drying said bibulous material.

The present invention is further directed to a dry indicator composition capable of exhibiting a sufficient color transition upon contacting a biological fluid test sample to demonstrate the presence or concentration of magnesium ions in the test sample comprising the components: (1) from 0.5% to 10% by weight of a dihydroxy complexometric dye; (2) from 0.5% to 10% by weight of a masking agent; (3) from 0.5% to 10% by weight of a stabilizer; (4) from 0.5% to 10% by weight of an alkaline buffer combination; (5) from 0.5% to 10% by weight of a chelating agent; and a bibulous material containing components (1), (2), (3), (4) and (5) dried thereon; and wherein the percent by weight of each component is based upon the total weight of the bibulous material dry reagent composition.

The present invention is based upon the discovery that dihydroxy complexometric dyes, preferably o,o'-dihydroxyarylazo compounds as complexometric dyes, were found to be especially suitable for medically important quantification of magnesium utilizing dry chemistry methods. These include Eriochrome® black T, Calmagite®, Magon®, hydroxynaphthol blue, arsenazo I, chlorophosphonazo III, and SPADNS. Specifically, these compounds are as follows:

1) Eriochrome® Black T:
   sodium 1-(1-hydroxy-2-naphthylazo)-6-nitro-2-naphthol-4-sulfonate
2) Calmagite®:
   1-(1-hydroxyl-4-methyl-2-phenylazo)-2-naphthol-4-sulphonic acid
3) Magon®:
   1-azo-2-hydroxy-3-(2,4-dimethyl-carbox-anilido)-naphthalene-1'-(2-hydroxybenzene)
4) Chlorophosphonazo III:
   2,7-bis(4-chloro-2-phosphonophenylazo)-1,8-dihydroxynaphthalene-3,6-disulfonic acid
5) Hydroxynaphthol blue:
   trisodium 1-(2-hydroxy-4-sulfo-1-naphthylazo)-2-naphthol-3,6-disulfonate
6) Arsenazo I:
   disodium 2-(4,5-dihydroxy-2,7-disulfo-3-naphthylazo)phenylarsonate
7) SPADNS:
   trisodium 3-(4-sulfophenylazo)-4,5-dihydroxy-2,7-naphthalenedisulfonate An effective amount of the complexometric dye ranges from 0.5% to 10% by weight based upon the total weight of the bibulous material dry indicator composition, and is preferably from 0.5% to 5% by weight. Calmagite® is especially preferred as the dihydroxyarylazo complexometric colored dye which is a chelatable reagent.

Paper-phase colorimetric test strips, first used in medicine with glucose determinations and quantified by eye or a dedicated reflectance photometer, have become a popular way for rapid testing of many analytes of medical interest. This method has the advantages of pre-measured reagents impregnated into the paper and a fixed amount of serum being tested, based on the volume absorbed by the test paper. With the addition of a semi-permeable membrane, blood cells do not have to be pre-separated from the serum to perform the test (see, for example, U.S. Pat. Nos. 3,092,465, 3,298,789 and 3,630,957).

It is common to include reagents in magnesium tests to mask out calcium as well as other heavy metals such as iron. The former is typically achieved with ethylene glycol bis(B-aminoethyl ether)-N,N'-tetraacetic acid (EGTA) and the latter with cyanide ion or triethanolamine. In that serum proteins bind to the complexometric dyes and shift their spectrum, surfactants able to form micelles are also typically added (see U.S. Pat. No. 3,754,864).

In the course of developing the present invention it was found that a major innovation was directed to the transferring of magnesium solution wet chemistry to the dry paper phase by overcoming the instability of the dye in an alkaline environment. In particular, soon after preparation of the dry test strips using reagent compositions found in the prior art, the characteristic blue color turned to dull red. This may have been due to carbon dioxide adsorption or oxidant interaction with the dye. It was unexpectedly discovered, for dry testing procedures of the present invention, that borate as a stabilizer could block this adverse side effect. An effective amount of the stabilizer ingredient which could be borate or aluminum hydroxide ranges from 0.5% to 10% by weight based upon the total weight of the dry indicator composition, and is preferably from 0.5% to 5% by weight, with borate being preferred.

This could not have been expected, even though complex bicyclic oxy-anions with 5-member rings containing 4-covalent boron (B), under wet chemical test conditions, are formed with some cisdiols such as catechol and mannitol.

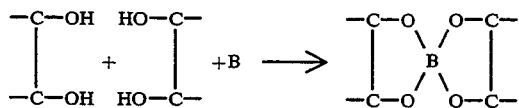

It is conceivable that such cyclic complexes are also formed between borate and the dihydroxy dyes employed here, and this stabilizes the dyes until they chelate with magnesium (M) in this test system.

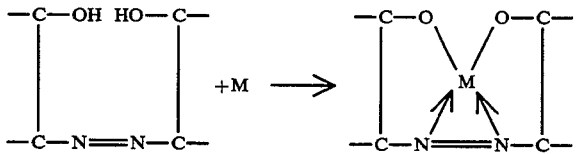

At the same time, borate/NaOH buffer provides the alkaline environment required by the complexometric reaction. Stabilization by dimethylsulfoxide, as disclosed in U.S. Pat. No. 4,383,043, was not applicable here since this reagent is a liquid at room temperature and would evaporate upon impregnation into a paper medium.

An additional unexpected result was that the application of a semipermeable membrane onto the dry test strip of the invention obviated the need to add a colloid to block the effect of serum proteins to the system. This was advantageous since polyvinylpyrrolidone, the most commonly used surfactant in the Calmagite ® method, was found to discolor the dye when dried together on paper. Furthermore, the use of triethanolamine salt of Calmagite ® eliminated the need to add the heavy metal masking agent separately.

Of the several dyes tested here, Calmagite ® (3-hydroxy-4-((2-hydroxy-5-methyl-phenyl)azo)-1-naphthalenesulfonic acid) has proven to be the preferred embodiment. With the improvements noted above, the combined dry chemistry system was stable on storage and provided reliable, reproducible results with standard and test serum specimens. A variation of the chelatometric method utilizes reactants, such o,o'-dihydroxyazobenzene, which forms fluorescent complexes with magnesium (Kaplan, L A, Pesce, A J, eds., *Clinical Chemistry*, C V Mosby Co., St. Louis, Mo., p. 1066, 1989). However, this approach is rarely used because it suffers from background fluorescence, interferences, delicate responses, and the need for sophisticated instrumentation.

Realizing that the most significant limiting factor in the o,o'-dihydroxyarylazo (e.g., Calmagite ®) wet testing method of magnesium determination is the instability of the reagent solution, numerous attempts have been made to overcome this problem of wet testing by adding or changing components of the wet test mixture (see U.S. Pat. Nos. 4,383,043, 4,454,230 and 4,503,156). Of even greater technical difficulty is utilizing this classical, well-established wet testing approach in a dry chemistry method. U.S. Pat. No. 4,753,890 confirms that "early attempts to assay liquids for magnesium ions with dry analytical elements were unsuccessful." This is taken to mean that Calmagite ® or related reagents could not be stabilized in the dry chemistry format. The latter patent therefore discards the established system and finds it necessary to utilize a totally different set of colorimetric reagents (2-hydroxy-substituted cyanoformazans) to make such a method feasible. Of further significance in the latter patent is that:

1) the method requires incubations of 37° F. and pipetting of microliter quantities of serum (not whole blood), thus removing it from the category of beside procedures, and 2) the test strips must be stored in a freezer before use and must be employed within 15 minutes of opening the package (Eastman Kodak Co. publication #C-349 (1991)).

In contradistinction, the stabilization method of the present invention has the advantage that it allows storage of dry test strips at room temperature before use with little loss of activity over several months. Once removed from their dry storage container, the test strips may be used in minutes or hours later, confirming the enhanced stability demonstrated by this method according to the present invention.

The wet solution methods currently available commercially using o,o'-dihydroxyarylazo color reagents in the prior art, give linear responses in the range of 0–3 meq/L (see, for example, Sigma Chem. Co. procedure pub. #595 (1985)). However, as noted earlier, it is often necessary, especially in the obstetrical situations cited, to quantify blood levels above 4 meq/L.

It is, therefore, a further object of the present invention to extend the level of linear sensitivity to include the higher range without loss of reactivity and stability, so as to obviate the need to dilute specimens before testing. It has unexpectedly been found that the addition of an effective amount of a chelating agent, preferably ethylene-diamine-tetraacetic acid (EDTA), produces successful results. The selection of EDTA as the chelating agent is particularly preferred based upon its newly discovered function to promote linearity in borate buffers simultaneously in combination with its stability constant with magnesium relative to calcium and the o,o'-dihydroxyarylazo compounds.

The chelating agent functions with compatibility with the agents within the bibulous material dry indicator composition. An effective amount of the chelating agent ranges from 0.5% to 10% by weight based upon the total weight of the bibulous material dry indicator composition, and is preferably from 0.5% to 5% by weight.

Furthermore, EDTA avoids interference with the masking function of EGTA on calcium. In this way, magnesium is chelated in concentrations up to 4 meq/L by the EDTA and is less available for reaction with the color reagent, which has a lower stability constant. Above this level, it was surprisingly found that the linear reactivity range of the complexometric reaction is extended to at least 10 meq/L. Furthermore, this desirable characteristic was also observed when the system was performed in the dry chemistry format.

An effective amount of the metal masking agent or agents ranges from 0.5% to 10% by weight based upon the total weight of the bibulous material dry indicator composition, and is preferably from 0.5% to 5% by weight. Suitable examples of the metal masking agent include cyanide, triethanolamine, and (EGTA) ethylene glycol bis(B-aminoethyl ether)-N,N'-tetraacetic acid. EGTA is the preferred masking agent for calcium. Triethanolamine is the preferred masking agent for iron.

Examples of the alkaline buffer include borate/KOH, borate/NaOH, ammonia/ammonium chloride, glycine/NaOH, 2-amino-2-methyl-1-propanol/NaOH, and 3-cyclohexyl-amino-1-propanesulfonic acid/NaOH of pH 10 or higher. An effective amount of the alkaline buffer ranges from 0.5% to 10% by weight based upon the total weight of the bibulous material dry indicator composition, and is preferably from 0.5% to 5% by weight.

The balance of the dry indicator composition test strip up to 100% by weight is the bibulous material based upon the total weight. Preferably, the bibulous material is filter paper.

The semipermeable membrane coating which covers and encapsulates the dry indicator test strip adds an additional amount of material which ranges from 20% to 70% by weight, preferably from 35% to 55% by weight, based upon total weight of the test strip.

Suitable chelating agents in addition to EDTA, which is ethylenediamine tetraacetic acid, include CyDTA, which is 1,2-cyclohexanediamine tetraacetic acid; DTPA, which is diethylene triamine pentaacetic acid; TTHA, which is triethylene tetramine hexaacetic acid; HEDTA, which is N-hydroxy ethylethylene-diamine triacetic acid; and NTA, which is nitrilotriacetic acid.

Examples of biological fluids which can be tested include whole blood, blood serum, blood plasma, amniotic fluid, urine, saliva, cerebrospinal fluid, sweat, stool extract, synovial fluid, tears and peritoneal fluid.

Other objects and features of the present invention will become apparent from the following detailed description considered in connection with the accompanying drawing and examples, which disclose several embodiments of the present invention. It should be understood, however, that the drawing is designed for the purpose of illustration only and not as a definition of the limits of the invention.

EXAMPLE 1

Figure 2:
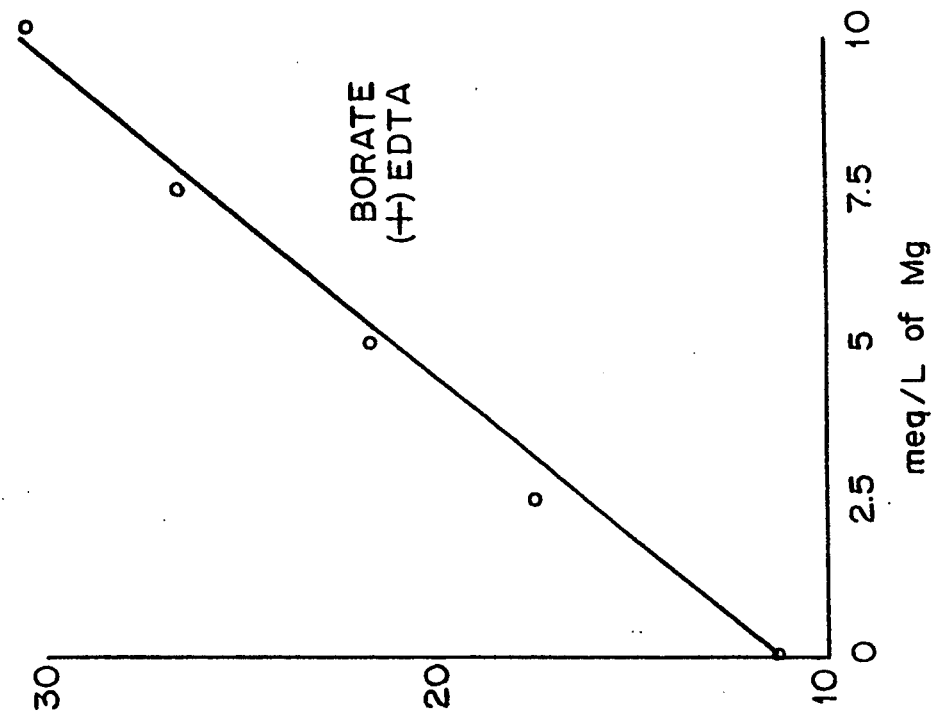
FIG. 2 shows Diascan® reflectance units versus magnesium concentration with borate and EDTA according to the invention (prepared as in embodiment Example 3).

A first embodiment of this magnesium test reagent strip uses a reagent solution made up of 373 mg KCl, 10 mg EGTA, 643 mg boric acid, 5.7 ml 1N NaOH, 4.3 ml distilled water, and 8 mg Calmagite®-triethanolammonium salt. This mixture is stirred until dissolved. A strip of Whatman #1 filter paper is immersed into the reagent solution until impregnation with the reagent solution, and is then dried in a stream of warm air. A coating solution of 50 mg ethyl cellulose is prepared in 5 ml of benzene. The test strip is then immersed into this coating solution until a semipermeable membrane coating is formed and again dried with a warm air stream. The test sample is applied to the dry indicator bibulous material reagent strip. After 10 seconds, the excess fluid is removed gently with a gauze pad and the optical density is read with a reflectance photometer at 530 nm. (The photometer used is the DIASCAN-S® Photometer, model 1250, manufactured by MIT Development Corp. of Norwalk, Conn.) Results are compared to values obtained with standard magnesium solutions. The remaining unused test papers are stored in a closed container with silicate dessicant.

EXAMPLE 2

A second embodiment of this magnesium test reagent strip uses a reagent solution made up of 375 mg KCl, 50 mg EGTA, 310 mg boric acid, 5 ml 1N NaOH, 45 ml distilled water and 40 mg Calmagite®-triethanolammonium salt. This mixture is stirred until dissolved. A strip of Whatman #54 filter paper is immersed into the reagent solution until impregnated with the reagent solution, and is then dried in a stream of warm air. A coating solution of 60 mg ethyl cellulose is prepared in 5 ml of ethyl acetate. The test strip is then immersed into the coating solution until a semipermeable membrane coating is formed and is again dried with a warm air stream. The test sample is applied to the dry indicator bibulous material reagent strip. After 90 seconds, the excess fluid is removed gently with a gauze pad, and the optical density is read with a reflectance photometer at 530 nm or at 640 nm. Results are compared to values obtained with standard magnesium solutions. The remaining unused test papers are stored in a closed container with silicate dessicant.

EXAMPLE 3

A third embodiment of this magnesium test reagent strip uses a reagent solution made up of 375 mg KCl, 50 mg EGTA, 93 mg sodium EDTA, 310 mg boric acid, 5 ml 1N NaOH, 45 ml distilled water, and 40 mg Calmagite®-triethanolammonium salt. The preparation procedure utilized is analogous to that in Example 2 above.

COMPARATIVE EXAMPLE 1

The loss of activity for Calmagite® (II) versus Xylidyl Blue® (I) in solution with the addition of the borate stabilizer of the invention, when stored in 0.1N NaOH at room temperature and measured by transmission spectrophotometry (using the Bausch & Lomb Spectronic 20 transmission spectrophotometer) at 600 nm, as shown in Table 1 (standardized to 100% on Day #0 in each case):

TABLE 1

| Day # | % Optical Density (I) Xylidyl Blue ® (with stabilizer) | % Optical Density II Calmagite ® (with stabilizer) |
| --- | --- | --- |
| 0 | 100 | 100 |
| 2 | 55 | 95 |
| 7 | 30 | 91 |

These results suggest that the interaction of Calmagite ® with borate stabilizer is sterically different from Xylidyl Blue ®. Thus, Tanaka could not render obvious the unexpectedly superior improvement of the present invention, since borate stabilization does not occur with the reagent of Tanaka. The optical density according to the instant invention stabilizes above 90 percent after 7 days, whereas in Tanaka the optical density decreases to 30 percent in seven days, or about one third that for the invention.

COMPARATIVE EXAMPLE 2

When the Calmagite ® solution is prepared without the borate stabilizer in 0.1N NaOH and stored at room temperature, optical density decreases rapidly, as shown in Table 2:

TABLE 2

| Day # | % Optical Density Calmagite ® (without stabilizer) | % Optical Density Calmagite ® (with stabilizer) |
| --- | --- | --- |
| 0 | 100 | 100 |
| 2 | 71 | 95 |
| 7 | 28 | 91 |

Strips were prepared as in embodiment Example 2 and were stored at 37° C. There is no measurable loss of activity when tested with a magnesium standard after 286 days. Strips prepared without the borate stabilizer decolorize soon after drying, so that no stability studies of them were necessary.

Taken together with Comparative Examples 1 and 2, these results show that in solution or dried on paper, Calmagite ® is not stable unless the borate stabilizer is added. When the stabilizer is added, the reagent strips remain stable for many months.

Figure 1:
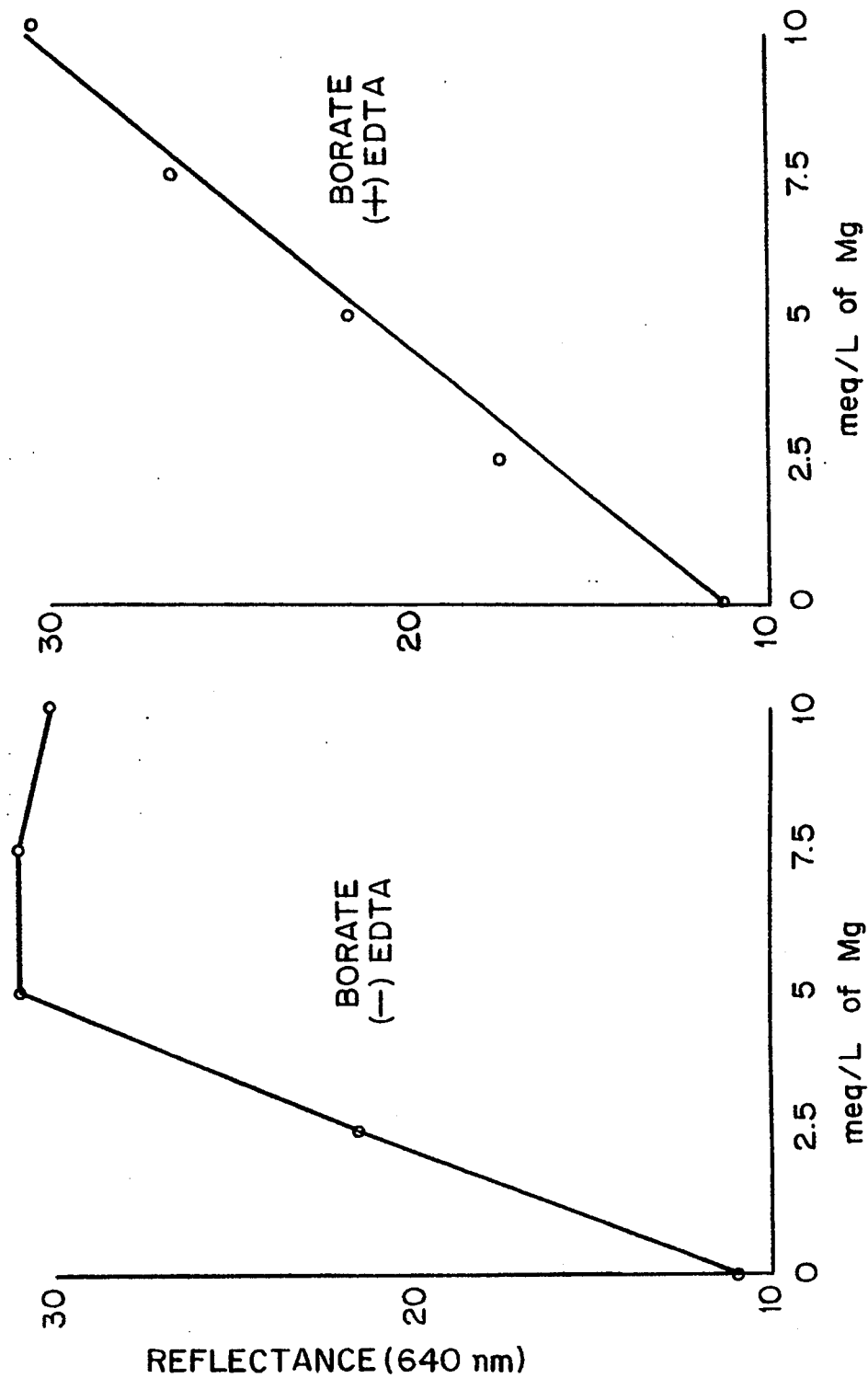
FIG. 1 shows Diascan® reflectance units versus magnesium concentration according to the invention with borate but without EDTA (prepared as in embodiment Example 2)

The wet solution methods currently available commercially using o,o'-dihydroxyarylazo color reagents in the prior art (see, for example, Sigma Chem. Co. procedure pub. #595 [1985]), as well as the dry chemistry method described in embodiment Example #2 only, give linear responses at or below 5 meq/L. (The latter is shown in FIG. 1 and is indicated by reflectance as a function of magnesium concentration as being linear up to 5.0 meq/L.) However, as noted earlier, it is often necessary, especially in the obstetrical situations cited, to quantify blood levels above 5 meq/L.

The chelating agent EDTA competes with the complexometric color reagent for magnesium. In this way, in the formulation described in Example #3, magnesium is masked in concentrations up to 5 meq/L by the EDTA and is less available for reaction with the color reagent, which has a lower stability constant. Above this level, it was surprisingly found that the complexometric color reaction occurs with a fixed extension of the linear reactivity range. Furthermore, this desirable characteristic was also observed when the system was performed in the dry chemistry format. This is shown in FIG. 2, wherein reflectance is a linear function of magnesium concientration up to 10 meq/L in the presence of EDTA.

While several examples of the present invention have been shown and described, it is to be understood that many changes and modifications may be made thereunto without departing from the spirit and scope of the invention as defined in the appended claims.

What is claimed is:

1. A process for measuring the magnesium concentration of a biological fluid test sample with a dry indicator bibulous material, comprising the steps of:
    a) providing a dry indicator bibulous material having predetermined effective amounts of a dihydroxy complexometric dye, a metal masking agent, a chelating agent and a dryable stabilizer in an alkaline buffer dried onto said material;
    b) providing a semipermeable membrane for said dry indicator bibulous material able to remove cells and large proteins from a test sample;
    c) contacting a biological fluid test sample with said dry indicator bibulous material;
    d) measuring the degree of color change of the dye in said dry indicator bibulous material due to the test sample;
    e) comparing the degree of color change against results with samples of known amounts of magnesium; and
    f) then determining the magnesium concentration of said biological fluid test sample.

2. The process according to claim 1, wherein step d) is carried out by comparison of the color produced with a standard color chart whose selected shades and intensities correspond to particular concentrations of magnesium.

3. The process according to claim 1, wherein step d) is carried out by measurement of the optical density by transmission or reflectance spectrophotometry.

4. The process according to claim 1, wherein said biological fluid being tested is selected from the group consisting of whole blood, blood serum, blood plasma, amniotic fluid, urine, saliva, cerebrospinal fluid, sweat, stool extract, synovial fluid, tears and peritoneal fluid.

5. The process according to claim 1, wherein said complexometric dye is a colored dihydroxyarylazo chelatable reagent selected from the group consisting of Calmagite ®, Eriochrome ® black T, Magon ®, hydroxynaphthol blue, arsenazo I, chlorophosphonazo III, and SPADNS.

6. The process according to claim 5, wherein said complexometric dye is Calmagite ®.

7. The process according to claim 1, wherein the alkaline buffer is selected from the group consisting of borate/KOH, borate/NaOH, ammonia/ammonium chloride, glycine/NaOH, 2-amino-2-methyl-1-propanol/NaOH, and 3-cyclohexyl-amino-1-propanesulfonic acid/NaOH of pH 10 or higher.

8. The process according to claim 1, wherein the stabilizer is borate.

9. The process according to claim 1, wherein the metal masking agent is selected from the group consisting of cyanide, triethanolamine, and ethylene glycol bis(B-aminoethyl ether)-N,N'-tetraacetic acid.

10. The process according to claim 1,
wherein the semipermeable membrane is selected from the group consisting of an organic polymer or a cellulose derivative.

11. The process according to claim 1,
wherein the chelating agent is selected from the group consisting of ethylenediamine tetraacetic acid (EDTA), diethylene triamine pentaacetic acid (DTPA), triethylene tetramine hexaacetic acid (TTHA), N-hydroxy ethylenediamine triaacetic acid (HEDTA), nitriloacetic acid (NTA), and 1,2-cyclohexanediamine tetraacetic acid (CYDTA).

12. A process for making a bibulous material dry indicator composition for measuring the magnesium concentration of a biological fluid in a dry chemistry procedure, comprising the steps of:
   a) preparing a reaction solution by supplying predetermined effective amounts of a dihydroxy complexometric dye, a masking agent, a chelating agent and a dryable stabilizer in an aqueous alkaline buffer;
   b) dipping the bibulous material into a reaction solution prepared as in step a);
   c) removing said bibulous material from said reaction solution;
   d) air-drying said treated bibulous material;
   e) dipping said bibulous material into an organic solution containing an organic polymer or cellulose derivative;
   f) removing said bibulous material from said organic solution; and
   g) air-drying said bibulous material.

13. A dry indicator composition capable of exhibiting a sufficient color transition upon contracting a biological fluid test sample to demonstrate the presence or concentration of magnesium ions in the test sample comprising the components:
   (1) from 0.5% to 10% by weight of a dihydroxy complexometric dye;
   (2) from 0.5% to 10% by weight of a masking agent;
   (3) from 0.5% to 10% by weight of a stabilizer;
   (4) from 0.5% to 10% by weight of an alkaline buffer;
   (5) from 0.5% to 10% by weight of a chelating agent; and
   (6) the balance of up to 100% by weight of a bibulous material containing components (1), (2), (3), (4) and (5) dried thereon; and
wherein the percent by weight of each component is based upon the total weight of the dry indicator composition.

14. The dry indicator composition of claim 13,
further comprising a semipermeable membrane encapsulating said bibulous material.

15. The dry indicator composition according to claim 14, wherein the semipermeable membrane is selected from the group consisting of an organic polymer or a cellulose derivative.

16. The dry indicator composition according to claim 13, wherein said complexometric dye is a colored dihydroxyarylazo chelatable reagent selected from the group consisting of Calmagite®, Ericchrome® black T, Magon®, hydroynaphthol blue, arsenazo I, chlorophosphonazo III, and SPADNS.

17. The dry indicator composition according to claim 16, wherein said complexometric dye is Calmagite®.

18. The dry indicator composition according to claim 13, wherein the alkaline buffer is selected from the group consisting of borate/KOH, borate/NaOH, ammonia/ammonium chloride, glycine/NaOH, 2-amino-2-methyl-1-propanol/NaOH, and 3-cyclohexyl-amino-1-propanesulfonic acid/NaOH of pH 10 or higher.

19. The dry indicator composition according to claim 13, wherein the stabilizer is borate.

20. The dry indicator composition according to claim 13, wherein the metal masking agent is selected from the group consisting of cyanide, triethanolamine, and ethylene glycol bis(B-aminoethyl ether)-N,N'-tetraacetic acid.

21. The dry indicator composition according to claim 13, wherein said chelating agent is selected from the group consisting of EDTA, CyDTA, DTPA, TTHA, HEDTA and NTA.

* * * * *